United States Patent
Huster et al.

(10) Patent No.: US 9,213,956 B2
(45) Date of Patent: Dec. 15, 2015

(54) ALGORITHM FOR PREDICTING AND MITIGATING ADVERSE EVENTS

(71) Applicant: Hill-Rom Services, Inc., Batesville, IN (US)

(72) Inventors: Keith A. Huster, Sunman, IN (US); Charles A. Lachenbruch, Lakeway, TX (US); Timothy J. Receveur, Guilford, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 152 days.

(21) Appl. No.: 13/793,848

(22) Filed: Mar. 11, 2013

(65) Prior Publication Data

US 2013/0246088 A1 Sep. 19, 2013

Related U.S. Application Data

(60) Provisional application No. 61/610,663, filed on Mar. 14, 2012.

(51) Int. Cl.
*G06Q 50/22* (2012.01)
*G06Q 10/06* (2012.01)
*G06F 19/00* (2011.01)

(52) U.S. Cl.
CPC ........ *G06Q 10/0635* (2013.01); *G06F 19/3406* (2013.01); *G06F 19/3468* (2013.01); *G06F 19/3481* (2013.01); *G06Q 50/22* (2013.01)

(58) Field of Classification Search
USPC ................ 705/2–3; 5/600; 340/573
See application file for complete search history.

(56) References Cited

U.S. PATENT DOCUMENTS

| | | | | |
|---|---|---|---|---|
| 7,746,218 B2* | 6/2010 | Collins, Jr. | ........... | A61B 5/1115 340/286.07 |
| 8,120,471 B2* | 2/2012 | Collins, Jr. | ........... | A61B 5/1115 340/286.07 |
| 8,266,742 B2* | 9/2012 | Andrienko | ............. | A61G 7/018 340/286.07 |
| 8,334,777 B2* | 12/2012 | Wilson | ................ | G05B 19/042 340/286.07 |
| 8,572,778 B2* | 11/2013 | Newkirk | ................ | A61G 7/018 5/600 |
| 8,620,682 B2* | 12/2013 | Bechtel | ................ | G06F 19/321 705/2 |
| 2008/0021731 A1* | 1/2008 | Rodgers | ............... | A61B 5/1113 705/2 |
| 2011/0120815 A1* | 5/2011 | Frolik | .................... | A61G 7/018 188/1.12 |
| 2011/0205061 A1* | 8/2011 | Wilson | ................. | G05B 19/042 340/573.1 |
| 2011/0231996 A1* | 9/2011 | Lemire | .................. | A61G 7/005 5/613 |
| 2014/0039351 A1* | 2/2014 | Mix | ..................... | A61B 5/1114 600/587 |

* cited by examiner

*Primary Examiner* — Michael Tomaszewski
(74) *Attorney, Agent, or Firm* — Barnes & Thornburg LLP

(57) ABSTRACT

A patient support apparatus includes a control system operable to gather physiological information about a patient supported on the patient support apparatus. The information may be gathered from sensors, a user interface, or a hospital information system. The control system also monitors operating parameters of the patient support apparatus and environmental conditions in the patient room. The control system utilizes the data gathered to identify a risk of an adverse event occurring to a patient supported on the patient support apparatus. The patient support apparatus is also operable to modify patient support apparatus parameters or environmental conditions to mitigate the risk of the adverse event.

23 Claims, 3 Drawing Sheets

ALGORITHM FOR PREDICTING AND MITIGATING ADVERSE EVENTS

CROSS-REFERENCE TO RELATED APPLICATIONS

The present application claims the benefit, under 35 U.S.C. §119(e), of U.S. Provisional Application No. 61/610,663, which was filed Mar. 14, 2012 and which is hereby incorporated by reference herein.

BACKGROUND

The present application is related to a patient support apparatus that includes a control system for predicting and mitigating events adverse to the health of a patient supported on the patient support apparatus. More specifically, the present application is directed to a patient support apparatus having a control system that gathers information regarding the patient supported on the apparatus, the environmental conditions in the room in which the patient support apparatus is located, and operational characteristics of the patient support apparatus and acts on that information to predict adverse patient events and mitigate those risks.

A patient in a care facility such as a hospital, for example, is often in a compromised medical condition and susceptible to developing complications. Injury sustained while in a care facility or the development of complications due to an extended presence in a care facility result in significant costs to the care facility and the patient. When these injuries or complications are considered preventable, the care facility acquired conditions may not be covered by a patient's insurer or other payers such as Medicare, for example. In an effort to prevent such injuries and complications, various protocols are implemented by the management of the care facilities to mitigate the risks. For example, the use of prophylactic antibiotics after surgery may be a standard institutional practice to mitigate the risk of surgical infections. Patients who are at risk of falling when moving unassisted may be identified as fall risks and certain protocols may be implemented to reduce the opportunity for the patient to move about the room unassisted.

In response to the desire of healthcare facilities to reduce risks, sensor systems to detect the status of various components of a patient support apparatus, such as a bed, for example, have been developed to help assure that protocols are being met. For example, patient position monitoring systems monitor the movement of a patient on a patient support apparatus and alarm if the movement is excessive or a patient has exited the bed. It is also known to implement alarms for certain bed positions, such as the amount of elevation of the head section of the bed to assure that a patient is positioned with her upper body at an appropriate angle relative to gravity when various therapies are being delivered. Also, the patient support apparatus may include sensors that detect when a side rail is in an appropriate position or that the brake system of the patient support apparatus is properly engaged. This information is provided to a central monitoring system, such as a nurse call system, so that deviations from the appropriate conditions may be monitored by the central system and alarms generated if a protocols are not being followed.

The use of these bed status variables requires that certain conditions be pre-established in the central monitoring system. For example, if the patient is a fall risk, the central monitoring system must be configured to monitor for side rail position and bed exit status for the particular patient support apparatus on which the fall risk patient is positioned. The same is true for other protocol monitoring conditions, the system must be configured for a particular patient, and the caregivers must modify the alarm conditions based on the particular protocols implemented for a given patient. Because of the required active intervention of the caregivers, protocols are often directed to particular classes of patients without regard to any patient or environmental based mitigating conditions. A change in status of a particular patient requires the caregiver to implement modified protocols and update any monitoring conditions that may need to be modified due to the change in the patient's condition.

Several conditions are of significant interest to caregivers based on the statistical incidence of care facility-based injuries or complications. For example, there is strong statistical support for a need to mitigate the risk of falls in patients who are 65 years or older. Other patient populations may also be at risk of falls depending on other medical conditions that are normally assessed at the time of admission into a care facility. However, as with any statistic, there are exceptions that mitigate the risk even in at risk populations. As a result, applying a "one-size-fits-all" fall prevention program based on age may not provide a patient who has a low risk with the appropriate care for that particular patient. A patient who has mitigating conditions which significantly reduce the risk of fall, even though their age places them in a high-risk group, may be negatively impacted in their recovery if the highest fall prevention protocol is applied to that particular patient. Generally, a fall prevention program requires a patient to be assisted when ambulating. For a patient who feels healthy and is at low risk of falling, such a protocol may result in the patient being noncompliant to other protocols.

Other risks include facility-acquired infections, such as infections acquired after a surgery. Patients who are positioned on the patient support apparatus for extended periods may also develop pressure ulcers on their skin. Various factors may result in a compromised skin condition that increases the potential of these nosocomial pressure ulcers. Another significant risk for bedridden patients is the development of Ventilator-Associated Pneumonia (VAP). Several factors may impact the likelihood of a particular patient acquiring a particular complication or suffering a particular injury while in a care facility.

SUMMARY

The present application discloses one or more of the features recited in the appended claims and/or the following features which alone or in any combination, may comprise patentable subject matter.

According to a first aspect of the present disclosure, a patient support apparatus comprises a plurality of sensors, a user interface including a plurality of input devices, a plurality of controllable devices, and a controller electrically coupled to the plurality of sensors and plurality of controllable devices. The controller includes a processor and a memory device electrically coupled to the processor. The memory device includes instructions that, when executed by the processor, cause the processor to process a plurality of data items related to physiological conditions of a patient associated with the patient support apparatus as detected by at least one of the plurality of sensors or the input devices. The processor analyzes the plurality of data items to determine a risk of an adverse event occurring to the patient.

In some embodiments, the memory device may further include instructions that, when executed by the processor, cause the processor identify at least one data item indicative of an environmental factor associated with the environment in which the patient support apparatus is located, analyze the plurality of data items related to the physiological conditions of the patient and the data item indicative of an environmental factor to determine the risk of an adverse event occurring to the patient.

In some embodiments, the memory device may further include instructions that, when executed by the processor, cause the processor to identify at least one data item indicative of a patient support apparatus factor associated with the patient support apparatus, analyze the plurality of data items related to the physiological conditions of the patient, the data item indicative of an environmental factor, and the data item indicative of a patient support apparatus factor to determine the risk of an adverse event occurring to the patient.

In some embodiments, the memory device may include instructions that, when executed by the processor, cause the processor to identify at least one data item indicative of a patient support apparatus factor associated with the patient support apparatus, analyze the plurality of data items related to the physiological conditions of the patient and the data item indicative of a patient support apparatus factor to determine the risk of an adverse event occurring to the patient.

In some embodiments, the memory device may further include instructions that, when executed by the processor, cause the processor to output a signal indicative of the risk of an adverse event occurring to the patient. The signal indicative of the risk of an adverse event occurring to the patient may cause the user interface to display an indication of the risk.

In some embodiments, the memory device may include instructions that, when executed by the processor, causes the processor to analyze the plurality of data items related to the physiological conditions of the patient, the data item indicative of an environmental factor, and the data item indicative of a patient support apparatus factor to determine if one or more of the data items are associated with a modifiable condition, and if one or more of the data items are modifiable, determine a value of a first one of the data items which will reduce the risk of an adverse event occurring to the patient.

In some embodiments, the memory device may include instructions that, when executed by the processor, causes the processor to alter the state of at least one of the controllable devices to alter the value of the first data item to the value of the first data item that reduces the risk of an adverse event occurring to the patient.

In some embodiments, the memory device may include instructions that, when executed by the processor, causes the processor determine a value of a second one of the data items which will reduce the risk of an adverse event occurring to the patient.

In some embodiments, the memory device may include instructions that, when executed by the processor, causes the processor to alter the state of at least one of the controllable devices to alter the value of the second data item to the value of the second data item that reduces the risk of an adverse event occurring to the patient.

In some embodiments, the memory device may further include instructions that, when executed by the processor, causes the processor determine a value for each of the data items which will reduce the risk of an adverse event occurring to the patient.

In some embodiments, the memory device may further include instructions that, when executed by the processor, causes the processor to alter the state of at least one of the controllable devices to alter the value of each of the data items to the value of each of the data items that reduces the risk of an adverse event occurring to the patient.

In some embodiments, the memory device may further include instructions that, when executed by the processor, causes the processor to generate a prompt at the display of the user interface indicating to a user the value of a first one of the data items necessary to reduce the risk of an adverse event occurring to the patient.

In some embodiments, the patient support apparatus includes a head section that is movable to change an attitude of the upper body of a patient supported on the patient support apparatus and at least one of the plurality of controllable devices is an actuator for controlling the attitude of the head section of the patient support apparatus.

In some embodiments, the control system analyzes the risk of ventilator-associated pneumonia, and, if the risk of ventilator-assisted pneumonia exceeds a predetermined threshold, the control system automatically operates the actuator to increase the attitude of the head section to exceed a minimum angle.

In some embodiments, the patient support apparatus may include a caster brake system that is movable between a locked state and an unlocked state and at least one of the plurality of controllable devices is an actuator for moving the caster brake system between the locked and unlocked states.

In some embodiments, the control system analyzes the risk of a patient fall, and, if the risk of patient fall exceeds a predetermined threshold, the control system automatically operates the actuator to move the caster brake system to a locked state.

In some embodiments, the patient support apparatus includes a siderail locking system that is movable between a locked state and an unlocked state and at least one of the plurality of controllable devices is an actuator for moving the siderail locking system between the locked and unlocked states.

In some embodiments, the control system analyzes the risk of a patient fall, and, if the risk of patient fall exceeds a predetermined threshold, the control system automatically operates the actuator to move siderail locking system to the locked state.

In some embodiments, the patient support apparatus includes a siderail actuation system that is operable to move at least one siderail between a lowered position and a raised position and at least one of the plurality of controllable devices is an actuator for moving the between the lowered and raised positions.

In some embodiments, the control system analyzes the risk of a patient fall, and, if the risk of patient fall exceeds a predetermined threshold, the control system automatically operates the actuator to move siderail to the raised position.

In some embodiments, the at least one of the plurality of controllable devices is a light controller operable to vary the operation of a light in the patient room between an illuminated and non-illuminated state.

In some embodiments, the control system analyzes the risk of a patient fall, and, if the risk of patient fall exceeds a predetermined threshold, the control system automatically modifies the light controller to illuminate the light.

In some embodiments, the patient support apparatus further comprises a surface including at least one bladder and at least one of the plurality of controllable devices is a surface pressurization system operable to vary the pressure in the at least one bladder and the control system analyzes the risk of a patient developing pressure ulcers, and, if the risk of developing pressure ulcers exceeds a predetermined threshold, the control system automatically modifies the operation of the surface pressurization system to vary the pressure in the at least one bladder to mitigate the risk of developing pressure ulcers.

According to a second aspect of the present disclosure, a patient support apparatus comprises at least one sensor, at least one component having multiple states, at least one actuator operable to vary the states of the at least one component, and a controller. The controller is operable to receive an input signal from the at least one sensor, the at least one signal including a first data item indicative of a physiological condition of a patient supported on the patient support apparatus and analyze the of data item to determine a risk of an adverse event occurring to the patient.

In some embodiments, the controller may be operable to determine if the risk of the adverse event exceeds a predetermined threshold.

In some embodiments, if the risk of the adverse event exceeds the predetermined threshold, the controller operates the at least one actuator to change the state of the component to reduce the risk of the adverse event.

In some embodiments, the component comprises a caster having a caster braking mechanism and the controller operates the actuator to move the caster braking mechanism into a state in which a caster brake is activated.

In some embodiments, the component comprises a siderail having a siderail locking mechanism and the controller operates the actuator to move the siderail locking mechanism into a state in which a siderail lock is activated.

In some embodiments, the component comprises a siderail having a siderail moving mechanism and the controller operates the actuator to move the siderail moving mechanism into a state in which the siderail is in a raised position.

In some embodiments, the component comprises a head section having head section moving mechanism and the controller operates the actuator to move the head section moving mechanism into a state in which the head section is raised beyond a minimum angle. In other embodiments, the controller operates the actuator to move the head section moving mechanism into a state in which the head section is raised below a maximum angle.

In some embodiments, the patient support apparatus further comprises a user interface including at least one input device and the controller is operable to receive a user input signal from the at least one input device, the user input signal including a second data item indicative of a physiological condition of a patient supported on the patient support apparatus, and analyze the first data item and second data item collectively to determine a risk of an adverse event occurring to the patient.

In some embodiments, the controller is operable to determine if the risk of the adverse event exceeds a predetermined threshold and if the risk of the adverse event exceeds the predetermined threshold, the controller operates the at least one actuator to change the state of the component to reduce the risk of the adverse event.

In some embodiments, the patient support apparatus includes a plurality of sensors, at least one of the plurality of sensors providing a signal including a second data item indicative of a patient support apparatus factor, and the controller is operable to analyze the first data item and second data item collectively to determine a risk of an adverse event occurring to the patient.

In some embodiments, the controller is operable to determine if the risk of the adverse event exceeds a predetermined threshold and if the risk of the adverse event exceeds the predetermined threshold, the controller operates the at least one actuator to change the state of the component to reduce the risk of the adverse event.

In some embodiments, the patient support apparatus includes a plurality of sensors, at least one of the plurality of sensors providing a signal including a second data item indicative of an environmental factor, and the controller is operable to analyze the first data item and second data item collectively to determine a risk of an adverse event occurring to the patient.

In some embodiments, the controller is operable to determine if the risk of the adverse event exceeds a predetermined threshold and, if the risk of the adverse event exceeds the predetermined threshold the controller operates the at least one actuator to change the state of the component to reduce the risk of the adverse event.

In some embodiments, the component comprises a light control device operable to change the state of a light that illuminates the room in which the patient support apparatus is positioned and the controller operates the at least one actuator to change the state of the light control device to turn the light on.

In some embodiments, the patient support apparatus includes a plurality of sensors, at least one of the plurality of sensors providing a signal including a second data item indicative of a second physiological condition of a patient supported on the patient support apparatus, and the controller is operable to analyze the first data item and second data item collectively to determine a risk of an adverse event occurring to the patient.

In some embodiments, the controller is operable to determine if the risk of the adverse event exceeds a predetermined threshold and if the risk of the adverse event exceeds the predetermined threshold, the controller operates the at least one actuator to change the state of the component to reduce the risk of the adverse event.

According to another aspect of the present disclosure, a patient support apparatus comprises at least one actuator operable to change the state of a component of the patient support apparatus, at least one input device, and a controller operable to receive a signal from the at least one input device, process the signal to determine the risk of an adverse event occurring to a patient supported on the at least one patient support apparatus, and if the risk of an adverse event exceeds a predetermined threshold, operate the actuator to change the state of the component to reduce the risk.

In some embodiments, the input device is a sensor that provides a signal related to a physiological condition of a patient supported on the patient support apparatus.

In some embodiments, the actuator activates a caster lock.

In some embodiments, the actuator activates a siderail lock.

In some embodiments, the actuator moves a siderail to a raised position.

In some embodiments, the actuator moves a head section of the patient support apparatus to an angle that exceeds a minimum threshold.

In some embodiments, the risk of the adverse event is determined using patient physiological data and at least one environmental factor collectively.

In some embodiments, the risk of the adverse event is determined using patient physiological data and at least one patient support apparatus factor collectively.

Additional features and advantages of the invention will become apparent to those skilled in the art upon consideration of the following detailed description of illustrated embodiments exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DRAWINGS

Figure 1:
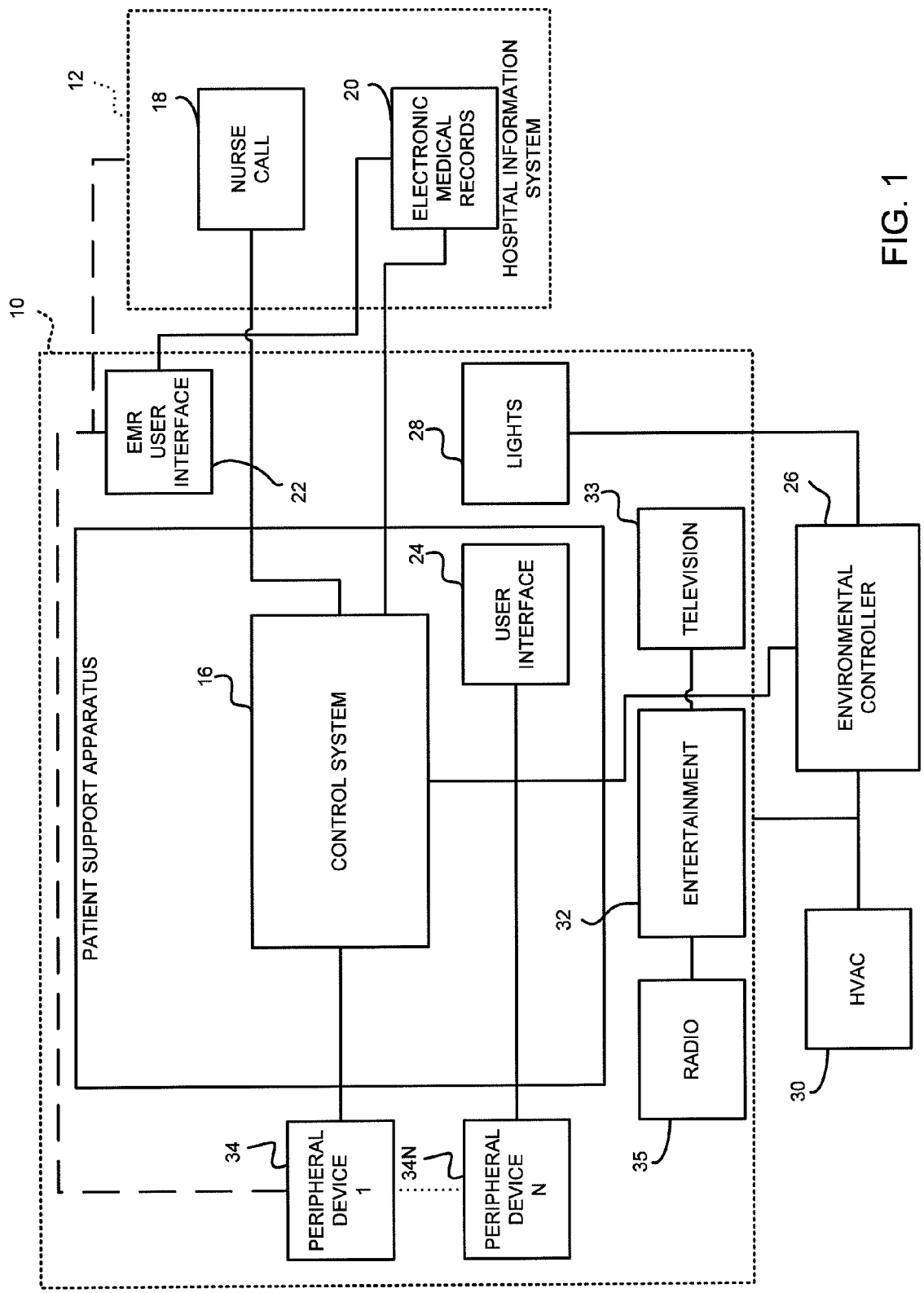
FIG. 1 is a diagrammatic view of a patient support apparatus positioned in a room, with a control system of the patient support apparatus in electrical communication with other devices, controllers, and systems positioned inside and outside the room.

The relationship between a patient support apparatus 14 positioned in a room 10 of a care facility and a hospital information system 12 is shown diagrammatically in FIG. 1. In the illustrative embodiment, the hospital information system 12 includes a centralized nurse call system 18 and a centralized electronic medical record system 20. Both the nurse call system 18 and electronic medical records system 20 include information that is related to a patient support apparatus 14 and associated with the patient stored in memory as related records. The information related to the patient stored in memory in the nurse call system 18 and electronic medical records system 20 is constantly updated as information is added to the electronic medical records system 20 and the nurse call system 18 receives information related to the patient and the patient support apparatus 14.

The patient support apparatus 14 includes a control system 16 that is in communication with the nurse call system 18. The control system 16 includes a user interface 24 that is used by the patient supported on the patient support apparatus 14 or a caregiver to provide inputs to the control system 16 or display outputs from the control system 16. As shown diagrammatically in FIG. 1, the electronic medical records system 20 is in electrical communication with a user interface 22 positioned in the room 10 and accessible by caregiver to input patient information and enter orders while the caregiver is in the room 10. The user interface 22 may be a personal computer or a dedicated peripheral device. It should be understood that other user interfaces may be used throughout a facility to interface with the hospital information system 12, and specifically the electronic medical records system 20. In the illustrative embodiment of FIG. 1, the user interface 24 is positioned on the patient support apparatus 14 and may be used by caregiver to access the electronic medical records system 20 through the control system 16 of the patient support apparatus 14, which is in direct communication with the electronic medical records system 20 and acts as a peripheral device to the electronic medical records system 20.

The control system 16 is also in communication with an environmental systems controller 26 which provides an interface between the patient support apparatus 14 and various environmental systems including lights 28, heating-ventilating-air-conditioning system 30, and entertainment devices 32 such as a television 33 or radio 35, for example. The environmental systems controller 26 provides information to the control system 16 and acts on instructions from the control system 16 to modify operation of the environmental systems. Some of the information provided by the environmental systems controller 26 is stored in memory associated with the environmental systems controller 26. The information provided by the environmental systems controller 26 is updated as operating parameters of the environmental systems change.

The control system 16 may also be in communication with one or more peripheral devices 34 positioned in the room 10. The peripheral devices 34 each perform a therapy or diagnostic function. For example, the peripheral device 34 may be a ventilator, heart monitor, blood pressure monitor, infusion device, blood oxygen monitor, sequential compression device, high-frequency chest wall oscillation device, or another standalone diagnostic or therapeutic device. Information used by the control system 16 may be stored in memory associated with a peripheral device 34, including the therapy parameters or current operating conditions of the peripheral device 34. In addition, diagnostic values such as a heart rate, blood pressure, or other diagnostic values may be stored in memory associated with the peripheral device. In some cases, the peripheral devices 34 may communicate to the controller 26 via a network connection such as a controller area network (CAN) and information stored on a controller of the device 34 may be accessible by the controller 26. In other cases, the information may be stored by the hospital information system 12. In still other cases, the peripheral devices 34 may communicate with the controller 26 and the controller 26 may store information related to the operator of the peripheral device(s) 34 in memory of the controller 26. As illustrated in FIG. 1, any number of peripheral devices 34 may be in communication with the patient support apparatus 14. It should be understood that peripheral devices such as the peripheral devices 34, may be in direct communication with the hospital information system 12 without being connected through the patient support apparatus 14.

The nurse call system 18 generates alarms and notifies caregivers of alarm conditions based on signals from the control system 16 of the patient support apparatus 14. It is also known in the art for the patient support apparatus 14 to provide a communication link such as audio or video communications between a patient supported on the patient support apparatus 14 and a nurse positioned at a central nurse call station 18. It is also known for caregivers to carry communication badges that include telephone or other voice communication capability, with the badges providing a direct communication between the caregiver and the central nurse call station 18 or patient, such as the system disclosed in U.S. Pat. No. 7,746,218 titled "Configurable System for Alerting Caregivers," incorporated by reference herein. The nurse call system and/or communication badges may facilitate direct communication between a caregiver and a patient positioned on any patient support apparatus is 14 throughout a care facility. In this way, the nurse call system 18 acts as a dispatch system to provide instructions to caregivers when various conditions warrant the intervention of the caregiver either to make adjustments to equipment or to respond to the needs of a particular patient.

Figure 2:
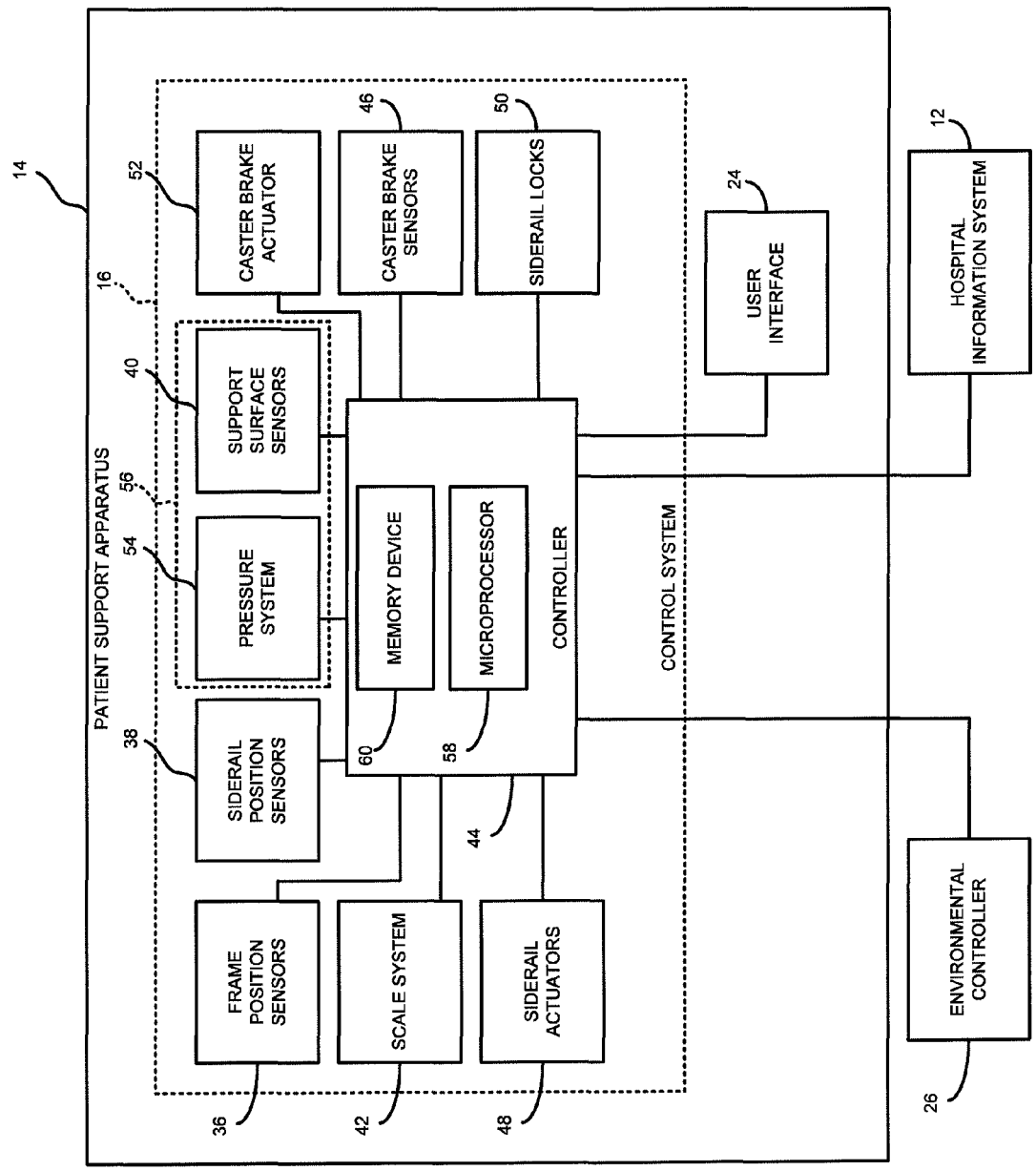
FIG. 2 is a diagrammatic representation of the electrical system of the patient support apparatus of FIG. 1.

The control system 16 of the patient support apparatus 14 includes input devices that provide information to a controller 44 of the control system 16. For example, referring to FIG. 2, frame position sensors 36, siderail position sensors 38, support surface sensors 40, a scale system 42, and caster brake sensors 46 are all in communication with the controller 44. The frame position sensors 36 provide information regarding the position of various components of the patient support apparatus 14. Information provided may include the height of the patient support apparatus 14, the inclination of a head section, the degree of tilt of an upper frame, or any other frame position data that might be available from frame position sensors 36 of the particular patient support apparatus 14.

The side rail position sensors 38 provide an indication to the controller 44 of whether a particular side rail of the patient support apparatus is in a raised or lowered position. It is contemplated that additional sensors may be implemented which indicate whether a particular side rail is latched into a particular position. The control system 16 includes siderail actuators 48, siderail locks 50, and caster brake actuators 52 which are each controlled by the controller 44. For example, the patient support apparatus 14 may include motorized side rails such as those disclosed in U.S. Patent Application Publication No. US 2009/0229051, titled "Siderail for a Patient-Support Apparatus," which is incorporated by reference herein. The patient support apparatus 14 may also include locking side rails that include an electromechanical lock, such as those disclosed in U.S. Patent Application Publication No. US 2009/0229051, with the lock retaining the side rail in a particular position. The siderail actuators 48 are operable to move the siderails between raised and lowered positions. The siderail locks 50 are operable to lock the siderail in a given position. The caster brake actuators 52 are operable to activate the caster brake system. For example, the caster brake actuators may actuate a locking mechanism. For example, the structures disclosed in U.S. Pat. No. 7,690,059 titled "Hospital Bed" or U.S. Pat. No. 7,200,894 titled "Roller," each of which is hereby incorporated by reference herein, disclose suitable locking mechanisms.

The support surface sensors 40 provide information regarding the operation of a support surface 56, such as an inflatable/pneumatic mattress, of the patient support apparatus 14. Such a support surface 56 may be integrated into the frame of the patient support apparatus 14 or may be a separate structure that is operated generally independently of the patient support apparatus 14, but communicates with the controller 44 of the patient support apparatus 14. The support surface sensors 40 may include pressure sensors that identify pressures in particular inflatable structures of the support surface or they may include position sensors. For example, accelerometers positioned in particular locations within the support surface 56 may provide feedback regarding the amount of inclination of a particular section of the support surface 56 relative to gravity, independent of the frame position sensors 36. The support surface sensors 40 may also provide information regarding the degree of lateral rotation of a patient supported on the support surface 56. In addition, the control system 16 includes a support surface pressure control system 54 which is operable to control the pressure in one or more air bladders in the support surface 56.

The scale system 42 provides information to the controller 44 regarding the weight of the patient supported on the patient support apparatus 14. The scale system 42 also provides information regarding the position of a patient on the patient support apparatus 14 and may provide information regarding the degree of movement of the patient. Such a system is disclosed in U.S. Pat. No. 5,276,432 titled "Patient Exit Detector Mechanism for Hospital Bed" or U.S. Pat. No. 7,437,787 titled "Load-Cell Based Hospital Bed Control," each of which is incorporated herein by reference. The data from the scale system 42 may also be used by the controller to determine if an unexpected weight has been added to the patient support apparatus 14 or provide other data regarding activities around the patient support apparatus 14. For example, in an approach disclosed in U.S. Published Pat. Application No. 2008/0189865 titled "System and Method for Controlling an Air Mattress," which is incorporated herein by reference, the support surface sensors 40 and the scale system 42 cooperate to provide data regarding the position of a patient supported on the patient support apparatus 14. For example, the support surface sensors 40 and scale system 42 may cooperate to determine that a patient is sitting up on a patient support apparatus 14 without having the head section raised as disclosed in U.S. Published Pat. Application No. 2008/0189865.

The caster brake sensors 46 provide information to the controller regarding the position of the brakes on the patient support apparatus 14. For example, casters should be in a locked position to prevent the bed from rolling as a patient attempts to exit the bed. In addition, activation or deactivation of the caster brake sensors 46 may provide an indication of the presence of a caregiver in the room 10 at a particular time. Activation of other caregiver controls may be considered to identify the presence of a caregiver in the patient room when the controls are activated.

It is within the scope of this disclosure for the patient support apparatus 14 to include other sensors that provide information to the controller 44 regarding the status of portions of the patient support apparatus 14 and the sensors discussed herein are examples only. In general, information that is related to the patient is considered to be physiological information, data items, or factors. This may include diagnostic or therapy information from a peripheral device 34, diagnoses or physical characteristics available from the electronic medical records system 20, including medications being taken or therapies being received, or patient specific information as detected by the scale system 42 or support surface sensors 40.

Information related to the patient support apparatus 14 is considered to be patient support apparatus information, data items, or factors. These include the positions of members or components of the patient support apparatus 14, the type of patient support apparatus, the status of patient support apparatus functions such as a caster lock or siderail lock.

Information related to the environment as determined and controlled by the environmental system 26 is considered to be environmental information, data items, or factors. This may include the status of various environmental equipment including room temperature, the status of lighting, the status of entertainment devices or other similar information.

Figure 3:
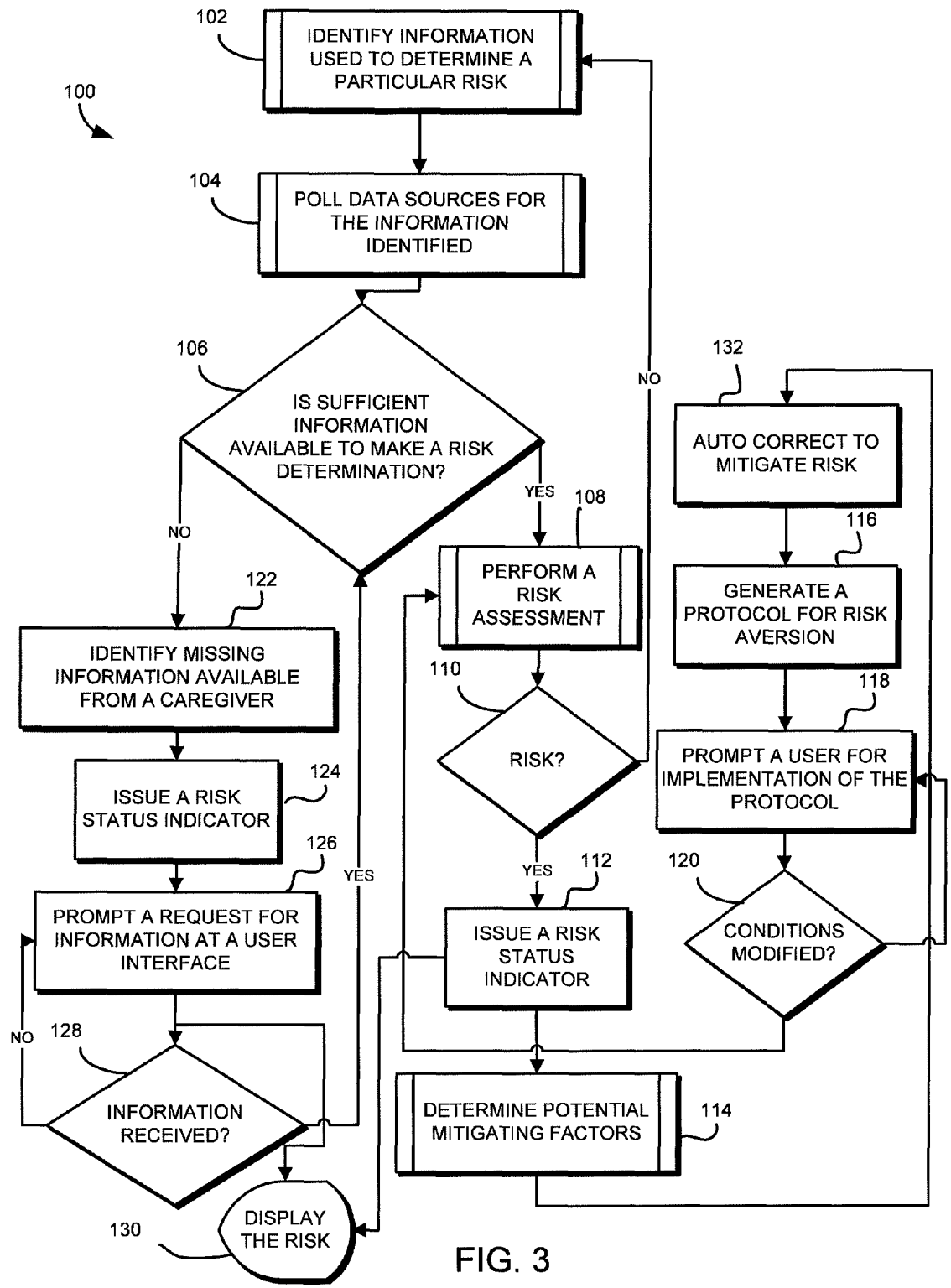
FIG. 3 is a flow chart of an algorithm for predicting and mitigating adverse events that may occur to a patient supported on the patient support apparatus of FIG. 1.

A generalized algorithm for predicting adverse events and mitigating the risk of adverse events is displayed graphically at FIG. 3. The algorithm 100 is performed by a processor 58 of the controller 44, utilizing instructions stored on a memory device 60 of the controller 44. The algorithm 100 is performed according to a preset schedule and initiated by a scheduler of the controller 44 at regular intervals, such as every 500 ms, for example. The algorithm 100 may be applied to multiple risks as will be discussed in further detail below. For example, the algorithm 100 may be applied to the risk of patient falls, risk of development of pressure ulcers, the risk of development of ventilator-associated pneumonia, or other risks that may be discerned from the information available in electronic medical record system, environmental operating conditions, and patient support apparatus operation variables.

It should be understood that information available to the control system 16 may be stored on memory associated with the peripheral devices 34, nurse call system 18, electronic medical records system 20, environmental system 26, or other similar devices or systems. In some embodiments, the control system 16 may receive information from each of the sources in real time and update the memory device 60 to include the most recent information available.

At an initial step 102, the controller 44 evaluates the information necessary to perform a risk analysis associated with a particular type of risk. The controller 44 also identifies the availability of the necessary information from the various sensors 36, 38, 40, 46, scale system 42, support surface pressure control system 54, caster brake actuators 52, siderail actuators 48, siderail locks 50, environmental systems 26, peripheral devices 34, and electronic medical records system 20 to determine the availability of information used to determine the particular risk. This information may vary from risk factor to risk factor, but may also include several common pieces of information as will be discussed in further detail below. Once the information that might be used to determine a particular risk is identified at step 102, at step 104 the controller 44 collects the available information from various data sources including the various sensors 36, 38, 40, 46, scale system 42, support surface pressure control system 54, caster brake actuators 52, siderail actuators 48, siderail locks 50, environmental systems 26, peripheral devices 34, and electronic medical records system 20.

The algorithm 100 then progresses to decision step 106 where the information that was collected from the data sources at step 104 is evaluated to determine if a statistically sufficient amount of information is available to determine the risk of a particular adverse event. The statistical sufficiency is predetermined from prior analyses of the information. For example, certain key pieces of information may always be required, such as the status of the siderails of the patient support apparatus 14 may be required for a fall risk analysis, for example. However, other information may be optional. There may also be a minimum of data items that may be used to perform the analysis. For example, in one illustrative embodiment, at least five data values must be present to perform the risk analysis. If there is insufficient data available to make a statistically valid evaluation of the risk, the algorithm 100 proceeds to step 122 where information that is missing may be available as an input from a caregiver is identified. The algorithm 100 then proceeds to step 124 where and indication of the risk status is issued to the system.

Depending on the circumstances, this risk status may be as simple as a message to the controller 44 that the risk of the particular adverse event is indeterminable, or the risk status indicator may provide information to the controller 44 which causes the controller 44 to generate an alarm. The response varies depending on the importance of the risk. Once the risk status indicator has been set at process step 124, the algorithm 100 proceeds to step 126 where the system prompts a request for information at a user interface 24. The risk is then displayed at step 130 and the algorithm 100 monitors inputs at step 128 to determine if any new information has been received. If no information has been received, the algorithm 100 loops back to step 126 and maintains the prompt for the request for information from the user at user interface 24. Thus, until the information necessary to properly assess the risk is entered, the risk is displayed as an out of acceptable condition at step 130. If however, new information is received at step 128, the algorithm 100 loops back to decision step 106 where the new information is evaluated to determine if sufficient information is available to make a risk determination.

If insufficient information is determined to be available at step 106, the algorithm 100 loops through again beginning at step 122 and maintains the display of the risk at step 130.

If sufficient information is available to make the risk determination at step 106, algorithm 100 proceeds to step 108 and performs a risk assessment. As will be described in further detail below, the risk assessment utilizes the information that is available to determine a level of risk, or risk score. The risk assessment will return a numerical risk score. The numerical risk score risk is evaluated at a decision step 110. At step 110, the numerical risk score is associated with a particular risk level. In some embodiments, if the risk score is greater than a threshold, the risk is determined to be excessive under a binary analysis. In other embodiments, the risk score may be categorized into one of multiple risk indication levels such as low, medium, or high. In some cases, the risk will be indicated to a user by a colored indicator, with green indicating low risk, yellow indicating medium risk, and red indicating serious risk, for example. If the risk is not determined to be excessive at step 110, the risk status is displayed at step 130 and the algorithm 100 is suspended until the algorithm 100 is processed again by the processor 58.

If the risk is considered to be excessive at step 110, the algorithm 100 proceeds to step 112 and issues a risk status indicator updating the display at step 130 and progressing to a step 114. At step 114 an analysis is performed to determine potential mitigating actions as will be described in further detail below. Part of the mitigation analysis at step 114 determines if there are factors that can be modified by the controller 44 to mitigate the risk. In addition, other factors that are independent of the control of the controller 44 that are identified as being excessive or out of an acceptable range are placed in an array. The algorithm 100 then proceeds to step 132 and automatically implements any corrective risk mitigation factors that might be available to the controller 44 to reduce the risk to an acceptable level.

The auto correct function at step 132 modifies of operating characteristics of the patient support apparatus 14 as necessary or available to mitigate the risks. For example, the controller 44 may engage the siderail locks 50 to secure a side rail in a raised position if such action would mitigate a fall risk identified by the algorithm 100. As used herein, the term "mitigate" means to reduce the risk score. Other automatically modifiable capabilities include modification of support surface pressure system 54 operating parameters to reduce the risk of development of pressure ulcers, or the modification of the position of a head section of the patient support apparatus 14 to mitigate the risk of the development of ventilator-associated pneumonia by raising the head section above a minimum threshold attitude or angle. The caster brakes may be engaged by the caster brake actuator 52. Siderails may be moved to a different position by a siderail actuator 48.

It should be understood that the auto correction/modification of operating parameters that has been described as occurring at step 132 may be optional or may be available for specific operational parameters only. In some embodiments, a user may program the control system 16 to prevent certain events from occurring automatically, based on user preferences. Once any available auto correction is completed at step 132, the algorithm 100 progresses to step 116 which generates an instruction to a caregiver to take an action to mitigate the risk. For example, the instruction may direct the caregiver to raise a side rail, lock the bed casters, modify the elevation of the patient support apparatus 14 or some portion of the patient support apparatus 14, or initialize a therapy, such as continuous lateral rotation therapy, for example. These are only examples of potential instructions that may be generated based on the risk identified. In such a case, the instructions may identify multiple actions to be undertaken by the caregiver and will identify the highest priority or largest impact modifications that can be made to mitigate the risk. The control system 16 provides information to the caregiver allowing the caregiver to select particular operating parameters to be modified so as to reduce the risk, at the discretion of the caregiver. The caregiver may prefer to implement to lower priority modifications to reduce the risk to an acceptable level as opposed to implementing the highest priority or most heavily weighted factor. For example, a particular patient may have a relatively minor fall risk that can be mitigated by lowering the bed height and raising a side rail. However, the caregiver may decide that for clinical reasons the preferred mitigation would be to activate a patient position monitoring function of the scale system 42 because the patient is relatively compliant but prefers to have the side rails down. If such modification will lower the risk score to an acceptable level, selective implementation of portions of the instruction may implemented to mitigate the risk.

Once the user has been prompted with instructions for risk mitigation at step 118, the algorithm 100 monitors the conditions identified in the instructions to determine if any of those conditions have been modified at step 120. If the conditions have been modified, algorithm 100 loops back to step 108 and re-initializes the risk assessment subroutine to determine if the modified conditions have reduce the risk to an acceptable level. If no conditions have been modified, the risk status continues to be displayed and the algorithm 100 loops back to step 118 and maintains a prompt for user to implement the instructions.

Information used to determine a risk score may include information that is available form the electronic medical record system 20, the environmental systems 26, one or more peripheral devices 34, or any of the sensors or systems associated with the patient support apparatus 14. The electronic medical record system 20 includes information that is entered as part of the admissions process and used by all caregivers to assess the mental and physical status of a patient. As this information has become more commonly available in electronic form, the ability of the controller 44 to access the available information increases the usefulness of the information.

For example, a common analysis used by caregivers is the Morse Fall Score which provides a numerical analysis of the risk of fall. The Morse Fall Score is based on six factors including the patient's history of falling, any secondary diagnosis related to falls, the type of intervention the patient requires, whether the patient has an IV or heparin lock, the patient's gait or ability to transfer to furniture, and the patient's mental status. Evaluating these factors using objective criteria returns numerical values that are accumulated to determine the overall Morse Fall Score. The Morse Fall Score is then used to determine the interventions necessary by caregivers in assuring that a patient is cared for in a way that mitigates fall risks. It is contemplated that each of the individual factors in the Morse Fall Score may be considered by an adverse event prediction algorithm to assess at least a portion of the likelihood that a particular patient may fall.

Other factors that may be considered include the extent of any cognitive impairment that a patient may suffer. An objective evaluation of the history of the patient including having the propensity to fall in the past may be used as a factor in consideration of a fall risk. Particular types of medications that the patient may be taking that affects their central nervous system may be assigned a numerical value. For example, a patient taking stimulants, antipsychotics, antidepressants, depressants, anticonvulsants, hallucinogens, or pain medications may indicate a fall risk. Any mobility impairments the patient may have may also be assessed and assigned a numerical score. For example, a patient who has had a joint replacement or who is a partial amputee may be assigned a mobility score that is less than optimal and may be considered in defining a fall risk.

The patient's age may also be a factor that is considered with the understanding that older patients are likely to suffer some impaired mobility. The patient's gender is also a factor to be considered as it is known that females are a higher fall risk under certain conditions as compared to males. Evidence of bowel or bladder incontinence may also be considered as a factor as this is likely to increase the urgency with which the patient may attempt to ambulate. Similarly, a patient who suffers postural hypotension exhibits an increased risk of falls. The patient's height and weight as individual values or the composite value of body mass index each may be considered in the assessment of the patient's fall risk under certain circumstances.

While the discussion of fall risk factors should not be considered comprehensive, it is clear that a significant amount of information that is available from a patient's medical record, and therefore the electronic medical record system, is useful in assessing a patient's risk of fall. Generally, many if not all of these factors are available in an electronic medical record maintained on electronic medical record system 20 and available to the controller 44.

In addition to the overall risk factors that are exhibited by a patient, the status of the patient support apparatus 14 on which the patient is supported and any other environmental conditions which are present, provide insight into the potential for the patient fall or provide a risk mitigation to prevent a patient from falling. To the extent that patient factors increase the risk of falls, certain bed parameters tend to reduce the potential for falls so that the comparison of those two factors may arrive at a risk of a particular patient falling at a particular time.

Some of the factors that may be considered when assessing risk of the patient fall include the height at which the bed is positioned and whether the side rails of the patient support apparatus 14 are raised. In addition, the status of a patient position monitoring system or bed exit system may also provide a measure of the likelihood of a patient falling without intervention by caregiver. Historical data from the patient position monitor is also useful in assessing the patient's risk of fall in that if the particular patient is causing the patient position monitoring system to alarm on a regular basis, it is indicative that the patient is noncompliant with whatever restrictions have been placed on the patient by the caregiver. Such an indication may be used to the discount certain factors, or reduce the weight of certain factors, if warranted.

Patient support apparatuses 14 that include a scale system may be operable to detect movement of the patient and establish a patient activity index that defines a patient fall risk parameter. While patient position monitoring systems are known to be predictive based on activities of a patient on the bed, the current position of the patient on the bed considered in conjunction with other risk factors and mitigation factors is a measure of the likelihood of the patient to fall. As discussed above, several approaches to determining the location of a patient on a patient support apparatus have been disclosed in the art.

Another factor that may be considered in determining the level of mitigation that has been implemented to reduce the likelihood of the patient fall includes the status of a bed monitoring system that provides an alarm if any of a group of preprogrammed parameters are not in compliance with the monitoring protocol. Yet another factor that may be considered is whether one or more of the bed operations are in a "locked out" status thereby preventing the patient from activating the functions. The status of any caster locking system is another factor which may be considered as a mitigation to patient falls.

The particular type of patient support apparatus may be yet another factor as the type of bed may increase the risk of patient falls as determined by some statistical analysis. Similarly, the type of patient support surface is being used may also provide mitigation factors or be statistically shown to have a higher incidence of patient falls. This may be due to the structure of the patient support surface such as having soft edges or other structures which make ingress from the patient support apparatus more difficult. Still another factor which may be considered is the state in which the patient support surface is operating, such as if the patient support surface is in a rotation mode resulting in discontinuities in the top surface of the patient support surface or movement of portions of the patient support surface.

The position of various members of the patient support apparatus may also be considered in the analysis of the patient's risk of falling. For example, if the patient support apparatus is in a chair configuration, the patient is more likely to attempt to egress from the patient support apparatus. Also, if a knee section or a head section of the patient support apparatus 14 is raised during the patient's egress, a patient's likelihood of falling may be increased due to the uneven surface Yet another factor to consider is the proximity of a caregiver to the patient support apparatus 14 as may be detected by the nurse call system 18. If the controller 44 identifies that a caregiver is present during the attempted egress, some of the factors of fall risk may be discounted, or the caregivers presence may be considered to be a mitigation. Other environmental conditions that may be detected by the controller 44 include the status of any room lighting. The controller 44 may be able to detect whether an overhead light is on in the room, and nightlight is on the patient support apparatus, indirect lighting being on in the room, or a reading light on the patient support apparatus being on. Similarly, the controller 44 may detect whether a television in the patient room is on and the status of the volume of the television. Also, the status of a radio or sound system in the room may be detected by the controller 44. In some situations, a television that is on or a radio that is on may lead to distraction to a patient who has a higher risk of fall such that the television activity or radio activity should be considered in the risk of fall analysis.

To the extent that the patient support apparatus 14 is in communication with any peripheral devices 34, the presence of the peripheral devices 34 may be considered in the risk of fall assessment. For example, if the controller 44 is aware that a blood oxygen saturation monitor is active, the presence of such a monitoring device may be considered a risk factor. A similar analysis is applicable to the presence of an infusion pump. Other devices that may be active include heart rate monitors, neurological monitors, ventilators, CPAP devices, drainage devices, would cure devices, sequential compression devices, or the like each of which may be detected by the patient support apparatus 14. In some instances, data from the peripheral devices 34 may be shared directly with the controller 44.

While many of the factors considered with regard to falls may also be considered with regard to VAP, there are other factors that may be considered as well. Pneumonia accounts for approximately 15% of all hospital acquired infections and 25% of all infections acquired in coronary care units and medical intensive care units (ICU) respectively. VAP, a serious subset of these hospital-acquired pneumonia infections, is the most common of all hospital-acquired infections which contribute to death mortality rate of approximately 30%.

VAP increases the patient's stay in the ICU, the overall length of hospital stay, and adds to overall costs. VAP is a bacterial pneumonia that develops in patients receiving mechanical ventilator support through an artificial airway. Early-onset pneumonia (those VAP cases that develop within the first 48 to 72 hours), is usually caused by one of the following bacteria: *staphylococcus aureus* (gram positive); *haemophilus influenzae* (gram negative); or *streptococcus pneumoniae* (gram positive). These are antibiotic sensitive strains which are common in the ICU. Late-onset VAP (cases that develop after 72 hours of ventilation) is usually caused by: methicillin resistant *staphylococcus aureus* (MRSA); *pseudomonas aeruginosa*; *acinetobacter* or *enterobacter*. In most patients, VAP is caused by multiple organisms.

VAP rates are reported as cases per 1000 ventilator days. The mean VAP rate for burn patients in the U.S. is 12.3. Neurosurgical patients have the highest rate at around 20 and pediatrics the lowest at 5.9. The overall percentages of hospital-acquired infections in U.S. hospitals rank urinary as the highest (31%), pneumonia second (27%), and blood stream third (19%). All three classes of infection are related to devices: urinary catheters, ventilators, and indwelling catheters, respectively.

Grossman reported that with each day of mechanical ventilation and intubation, the crude VAP rate increases by 1% to 3% and the death risk increases from two-fold to 10-fold (Grossman R F, Fein A. Evidence-Based Assessment of Diagnostic Tests for Ventilator-Associated Pneumonia: Executive Summary. *Chest* 2000; 117:177 S-181).

The single largest VAP risk factor is the endotracheal tube. Because mechanical ventilator support cannot be performed without the endotracheal tube (or other artificial airway), it is a necessary danger. The endotracheal tube provides a direct passageway into the lungs, bypassing many "natural protection" mechanisms. The endotracheal tube increases the risk for VAP by preventing cough and upper airway filtering. VAP also prevents upper airway humidification and inhibiting epiglottic and upper airway reflexes. The VAP acts as a direct conduit into the lungs for airborne pathogens and potentially acts as a reservoir for pathogens by providing a place for biofilm to form. The VAP inhibits cilliary transport by the epithelium requires a cuff which provides a place for secretions to "pool" in the hypoglottic area. The VAP also initiates a foreign body reaction, thereby interfering with the local immune response.

Risk factors that may be considered include a patient age of 65 or more. Also, some underlying chronic illness (e.g. Chronic Obstructive Pulmonary Disease (COPD), emphysema, asthma) or diseases causing immunosuppression increase risks. A patient who is unconscious or suffers depressed consciousness has a higher risk of VAP. Additional factors that increase the risk of VAP include: thoracic or abdominal surgery; previous antibiotic therapy; and previous pneumonia or remote infection.

Other device treatment and personnel related risk factors include: nasogastric tube placement; bolus enteral feeding; gastric over-distension; stress ulcer treatment; a supine patient position; nasal intubation; and nonconformance to hand-washing protocol. Still other patient factors that may be considered in determining risk include the patient's perfusion ratio, the patient's $SpO_2$ measurement, the presence of acute respiratory distress syndrome, ongoing medications such as sedatives or antibiotics, or the number of previous intubations. The presence of gastric tubes or the use of enteral feedings increases VAP risk as well. There are standard measures of risk that may also be considered including the Predicus™ Risk Score, for example.

To mitigate VAP, it is important that foreign material is not allowed to enter the lungs. This is ensured primarily via regular suction and oral hygiene. The primary patient support apparatus mitigation is to maintain the head of bed angle (HOB) to 30 degrees or more. Supine body position is a risk factor for VAP. Elevation of the head of the bed to 30 degrees is strongly supported as a low cost preventive strategy that lowers the risk of aspiration.

Additional mitigations of VAP may be documented in the electronic medical record system 20 and considered in the risk analysis. For example, documentation that care was used to ensure that secretions are not allowed to spread, such as hand-washing and the use of gowns and gloves may be considered. The completion of suction and oral cleaning processes should be documented as well and may be considered in the risk analysis.

Some of the risk factors that may indicate a fall risk or the risk of development of VAP may also be used to determine the risk of a patient developing pressure ulcers, also known as bed sores. Risk factors, in addition to some of those previously discussed, that may indicate a propensity for the development of pressure ulcers include fecal incontinence, excessive skin moisture, low diastolic blood pressure, a history of smoking, and body temperature. Each of these factors may be an indicator of the risk of developing pressure ulcers on the skin. Gender is also a factor with men having a higher propensity for skin breakdown. A lack of sensory perception limits the patient's ability to feel the development of a skin injury and may be used by an algorithm to indicate a higher risk of development of pressure ulcers. A lack of mobility is an additional risk factor. Poor nutrition is still another factor. In some cases, patient mobility may be monitored and excessive time in a single position may be defined as a risk factor that is then used to prompt movement of the patient by caregiver or adjustment of pressure in an inflatable patient support surface. Also, unacceptable levels of skin moisture or skin temperature, or a combination thereof, may be identified as a risk factor that may be modified by changing the operation of the patient support surface such as by increasing or reducing a flow of air to the patient interface to increase or decrease evaporation. Thus, excessively dry or moist skin can be addressed. Also, skin temperature may be modified by cooling the patient interface, cooling air flowing to the patient interface, heating the patient interface, or heating air flowing to the patient interface.

Non-patient factors may include excessive interface pressure between a patient's skin and a patient support surface. Other factors include the temperature of the patient support surface and shear or friction between the patient and the support surface. The shear/friction factor may be considered as a part of a broader statistical application of risk based on the type of support surface being used.

The algorithm 100 includes several process steps but relies on the availability of at least a minimum of information to perform the risk analysis. Each factor described above is a potential data point in the analysis and the algorithm 100 is configured to use the available data to perform the analysis, if a minimum amount of data required to perform the analysis with statistical significance is available.

Depending on the algorithm used, each factor has coefficient that is applied to the factor multiplied by the factor value. Some factors have a value that is normalized to be used in the risk calculation. Other factors have a discrete integer value of that is entered depending on the condition. Still other factors have a binary value of either being true or false.

As a baseline, for example, the risk analysis may require a minimum of five factors be available to perform the risk analysis. The number of factors available may be increased or decreased depending on the particular risk being analyzed and the statistical significance of the factors. In one embodiment, the risk is calculated according to the following generalized equation:

$$\text{RISK} = \sum_{1}^{n} \frac{C_x F_x}{n}; \quad \text{Equation (1)}$$
$$n > 4$$

where: C is the coefficient for a factor x and F is the value for the factor x. Each coefficient C may be any real number and is selected in an effort to normalize the associated factor F to a relative value that provides a risk score related to that factor. Thus, for each of at least five factors, because n must be greater than 4, each factor is calculated to a normalized risk value. Each risk value is then discounted by the total number of risk values available for consideration. If the calculated risk is greater than 1, then a risk condition exists and should be addressed. It should be understood that for factors that have a negative correlation to risk, the coefficient $C_x$ is a negative number, thereby reducing the overall score. While the number of factors in the illustrative embodiment is greater than four, it should be understood that in some embodiments a fewer number of factors may be considered, so long as sufficient statistical significance can be applied to the analysis.

In another embodiment, the risk score sensitivity may be refined by eliminating the discounting of the normalized score by the number of samples and applying a sample-size based coefficient to each factor as shown in Equation 2 below:

$$\text{RISK} = \Sigma_1^n C_{x_n} F_x; \, n>4 \quad \text{Equation (2)}$$

where: C is the coefficient for a factor x when the number of factors available is n and F is the value for the factor x. For factors that have a negative correlation to risk, the coefficient $C_x$ is negative number, thereby reducing the overall score. With Equation 2, the coefficient normalizes the factor to account for the sample size so that the factor is properly weighted.

The approach of Equation 2 permits strongly correlative factors to be weighted heavily and factors that correlate less strongly to be weighted at lightly. It should be understood that any of a number of approaches may be applied to weight the different factors that affect the risk of an adverse event occurring. Determination of the factors to be used and the weighting of the factors may vary from application to application. For example, the patient's weight may be considered as a factor in both the analysis of fall risk and the analysis of the risk of developing bed sores. However, the coefficients of weight are likely to be different in each risk analysis.

Although the invention has been described with reference to the disclosed embodiments, variations and modifications exist within the scope and spirit of the invention as described and defined in the following claims.

The invention claimed is:
1. A patient support apparatus comprising
a plurality of sensors,
a user interface including a plurality of input devices,
a plurality of controllable devices, and
a controller electrically coupled to the plurality of sensors and plurality of controllable devices, the controller including a processor and a memory device electrically coupled to the processor, the memory device including instructions that, when executed by the processor, cause the processor to process a plurality of data items related to physiological conditions of a patient associated with the patient support apparatus as detected by at least one of the plurality of sensors or the input devices and analyze the plurality of data items to determine a risk of an adverse event occurring to the patient, wherein the patient support apparatus includes a siderail locking system that is movable between a locked state and an unlocked state and at least one of the plurality of controllable devices is an actuator for moving the siderail locking system between the locked and unlocked states, wherein the controller operates the actuator for moving the siderail locking system to move the siderail locking system to the locked state when the risk of a patient fall exceeds a threshold as determined by the controller when the plurality of data items is analyzed.

2. The patient support apparatus of claim 1, wherein the memory device further includes instructions that, when executed by the processor, cause the processor identify at least one data item indicative of an environmental factor associated with the environment in which the patient support apparatus is located, analyze the plurality of data items related to the physiological conditions of the patient and the data item indicative of an environmental factor to determine the risk of an adverse event occurring to the patient.

3. The patient support apparatus of claim 2, wherein the memory device further includes instructions that, when executed by the processor, cause the processor to identify at least one data item indicative of a patient support apparatus factor associated with the patient support apparatus is located, analyze the plurality of data items related to the physiological conditions of the patient, the data item indicative of an environmental factor, and the data item indicative of a patient support apparatus factor to determine the risk of an adverse event occurring to the patient.

4. The patient support apparatus of claim 1, wherein the memory device further includes instructions that, when executed by the processor, cause the processor to identify at least one data item indicative of a patient support apparatus factor associated with the patient support apparatus, analyze the plurality of data items related to the physiological conditions of the patient and the data item indicative of a patient support apparatus factor to determine the risk of an adverse event occurring to the patient.

5. The patient support apparatus of claim 4, wherein the memory device further includes instructions that, when executed by the processor, cause the processor to output a signal indicative of the risk of an adverse event occurring to the patient.

6. The patient support apparatus of claim 5, wherein the signal indicative of the risk of an adverse event occurring to the patient causes the user interface to display an indication of the risk.

7. The patient support apparatus of claim 4, wherein the memory device further includes instructions that, when executed by the processor, causes the processor to analyze the plurality of data items related to the physiological conditions of the patient, the data item indicative of an environmental factor, and the data item indicative of a patient support apparatus factor to determine if one or more of the data items are associated with a modifiable condition, and if one or more of the data items are modifiable, determine a value of a first one of the data items which will reduce the risk of an adverse event occurring to the patient.

8. The patient support apparatus of claim 7, wherein the memory device further includes instructions that, when executed by the processor, causes the processor to alter the state of at least one of the controllable devices to alter the value of the first data item to the value of the first data item that reduces the risk of an adverse event occurring to the patient.

9. The patient support apparatus of claim 8, wherein the memory device further includes instructions that, when executed by the processor, causes the processor determine a value of a second one of the data items which will reduce the risk of an adverse event occurring to the patient.

10. The patient support apparatus of claim 9, wherein the memory device further includes instructions that, when executed by the processor, causes the processor to alter the state of at least one of the controllable devices to alter the value of the second data item to the value of the second data item that reduces the risk of an adverse event occurring to the patient.

11. The patient support apparatus of claim 7, wherein the memory device further includes instructions that, when executed by the processor, causes the processor determine a value for each of the data items which will reduce the risk of an adverse event occurring to the patient.

12. The patient support apparatus of claim 11, wherein the memory device further includes instructions that, when executed by the processor, causes the processor to alter the state of at least one of the controllable devices to alter the value of each of the data items to the value of each of the data items that reduces the risk of an adverse event occurring to the patient.

13. The patient support apparatus of claim 7, wherein the memory device further includes instructions that, when executed by the processor, causes the processor to generate a prompt at the display of the user interface indicating to a user the value of a first one of the data items necessary to reduce the risk of an adverse event occurring to the patient.

14. The patient support apparatus of claim 1, wherein the patient support apparatus includes a head section that is movable to change an attitude of the upper body of a patient supported on the patient support apparatus and at least one of the plurality of controllable devices is an actuator for controlling the attitude of the head section of the patient support apparatus.

15. The patient support apparatus of claim 14, wherein the controller analyzes the risk of ventilator-associated pneumonia, and, if the risk of ventilator-assisted pneumonia exceeds a predetermined threshold, the controller automatically operates the actuator to increase the attitude of the head section to exceed a minimum allowable angle.

16. The patient support apparatus of claim 1, wherein the patient support apparatus includes a caster brake system that is movable between a locked state and an unlocked state and at least one of the plurality of controllable devices is an actuator for moving the caster brake system between the locked and unlocked states.

17. The patient support apparatus of claim 16, wherein the controller analyzes the risk of a patient fall, and, if the risk of patient fall exceeds a predetermined threshold, the controller automatically operates the actuator to move the caster brake system to a locked state.

18. The patient support apparatus of claim 1, wherein the controller analyzes the risk of a patient fall, and, if the risk of patient fall exceeds a predetermined threshold, the controller automatically operates the actuator to move siderail locking system to the locked state.

19. A patient support apparatus comprising
a plurality of sensors,
a user interface including a plurality of input devices,
a plurality of controllable devices, and
a controller electrically coupled to the plurality of sensors and plurality of controllable devices, the controller including a processor and a memory device electrically coupled to the processor, the memory device including instructions that, when executed by the processor, cause the processor to process a plurality of data items related to physiological conditions of a patient associated with the patient support apparatus as detected by at least one of the plurality of sensors or the input devices and analyze the plurality of data items to determine a risk of an adverse event occurring to the patient, wherein the patient support apparatus includes a siderail actuation system that is operable to move at least one siderail between a lowered position and a raised position and at least one of the plurality of controllable devices is an actuator for moving the siderail between the lowered and raised positions, wherein the controller operates the actuator for moving the siderail to move the siderail to the raised position when the risk of a patient fall exceeds a threshold as determined by the controller when the plurality of data items is analyzed.

20. The patient support apparatus of claim 19, wherein the controller analyzes the risk of a patient fall, and, if the risk of patient fall exceeds a predetermined threshold, the controller automatically operates the actuator to move siderail to the raised position.

21. The patient support apparatus of claim 1, wherein the at least one of the plurality of controllable devices is a light controller operable to vary the operation of a light in the patient room between an illuminated and non-illuminated state.

22. The patient support apparatus of claim 21, wherein the controller analyzes the risk of a patient fall, and, if the risk of patient fall exceeds a predetermined threshold, the controller automatically modifies the light controller to illuminate the light.

23. The patient support apparatus of claim 1, wherein the patient support apparatus further comprises a surface including at least one bladder and at least one of the plurality of controllable devices is a surface pressurization system operable to vary the pressure in the at least one bladder and the controller analyzes the risk of a patient developing pressure ulcers, and, if the risk of developing pressure ulcers exceeds a predetermined threshold, the controller automatically modifies the operation of the surface pressurization system to vary the pressure in the at least one bladder to mitigate the risk of developing pressure ulcers.

* * * * *